US00PP35660P2

(12) United States Plant Patent
Van Swieten

(10) Patent No.: US PP35,660 P2
(45) Date of Patent: Feb. 20, 2024

(54) ***PHALAENOPSIS* ORCHID PLANT NAMED 'PHA777638'**

(50) Latin Name: ***Phalaenopsis* hybrid**
Varietal Denomination: PHA777638

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,296

(22) Filed: Jun. 22, 2023

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHA777638', particularly characterized by having numerous, attractive purplish-pink flowers with reddish-purple lips, flowers that are flat in lateral view, and strong lip curvature of lateral lobes, is disclosed.

3 Drawing Sheets

Genus and species: *Phalaenopsis* hybrid.
Variety denomination: 'PHA777638'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA777638'.

The new *Phalaenopsis* plant is a product of a planned breeding program conducted by the inventor in Bleiswijk, the Netherlands. The objective of this breeding program was to create a new *Phalaenopsis* plant with numerous, attractive purplish-pink flowers with reddish-purple lips suitable for potted plant production.

The new *Phalaenopsis* plant 'PHA777638' is a result of cross-pollination made by the inventor in March 2015 in Bleiswijk, the Netherlands, of the proprietary female, or seed parent, *Phalaenopsis* hybrid '00001-4992' (unpatented), with a proprietary male, or pollen parent, *Phalaenopsis* hybrid 'PHALLOEL' (unpatented).

The new *Phalaenopsis* was selected by the inventor as a single plant within the progeny of the stated cross-pollination in a controlled, greenhouse in Bleiswijk, the Netherlands, in December 2017. Asexual reproduction of the new *Phalaenopsis* plant by meristem tissue culture since 2019 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 20, 2022 (Application No. 2022/1060), by Applicant who obtained the subject matter disclosed directly from the inventor. 'PHA777638' has not been made publicly available or sold anywhere in the world prior to the effective filing date of this application with the exception of sales or disclosures made one year or less before the effective filing date of this claimed invention by Applicant who obtained 'PHA777638' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA777638' as a new and distinct variety of *Phalaenopsis* plant:

1) Purplish-pink flowers with reddish-purple lips;
2) Flower shape in lateral view is flat; and
3) Lip curvature of lateral lobe is strong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2023. Colors in the photographs may differ from the color values cited in the detailed botanical description, which accurately describe the actual colors of the new variety.

DESCRIPTION OF THE NEW VARIETY

Figure 1:
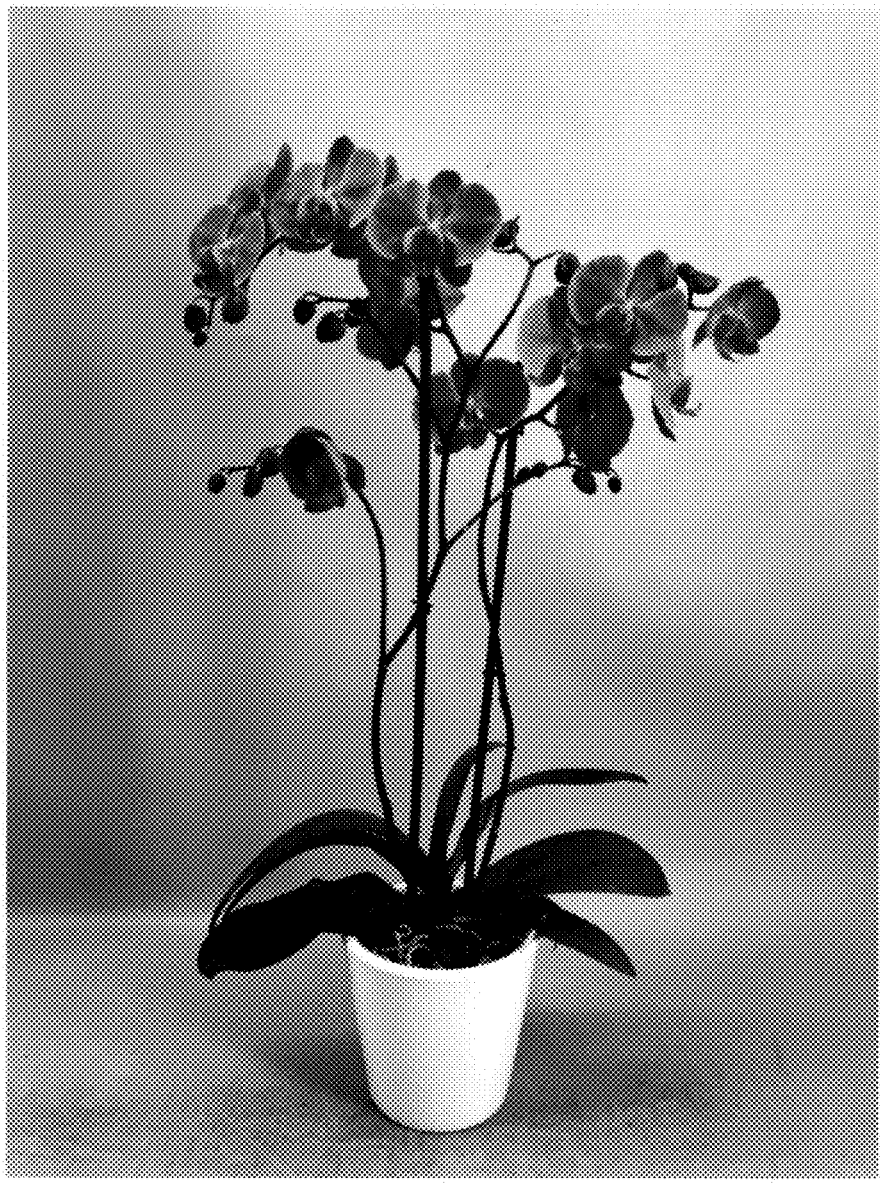
FIG. 1 shows the overall plant habit, including blooms, buds, and foliage of 'PHA777638'.
Figure 2:
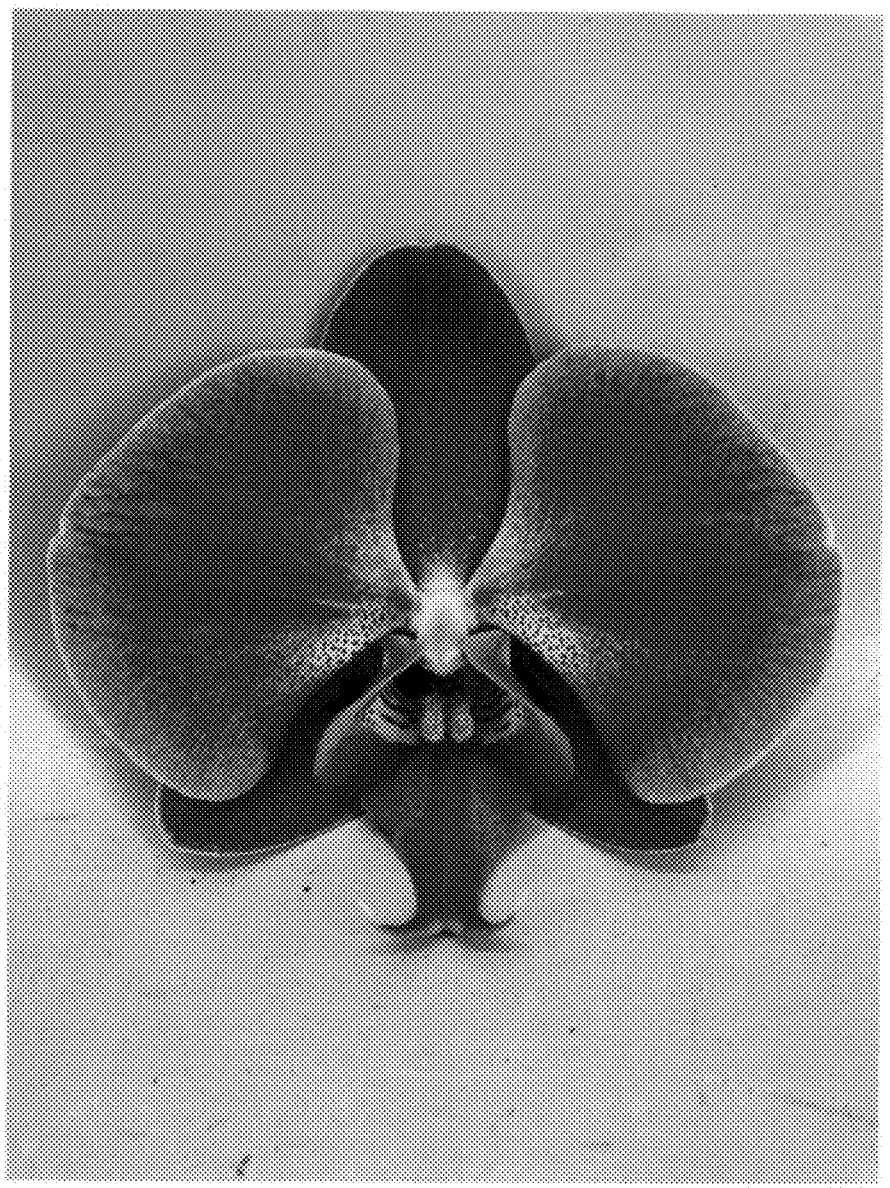
FIG. 2 shows a close-up of a flower of 'PHA777638'.
Figure 3:
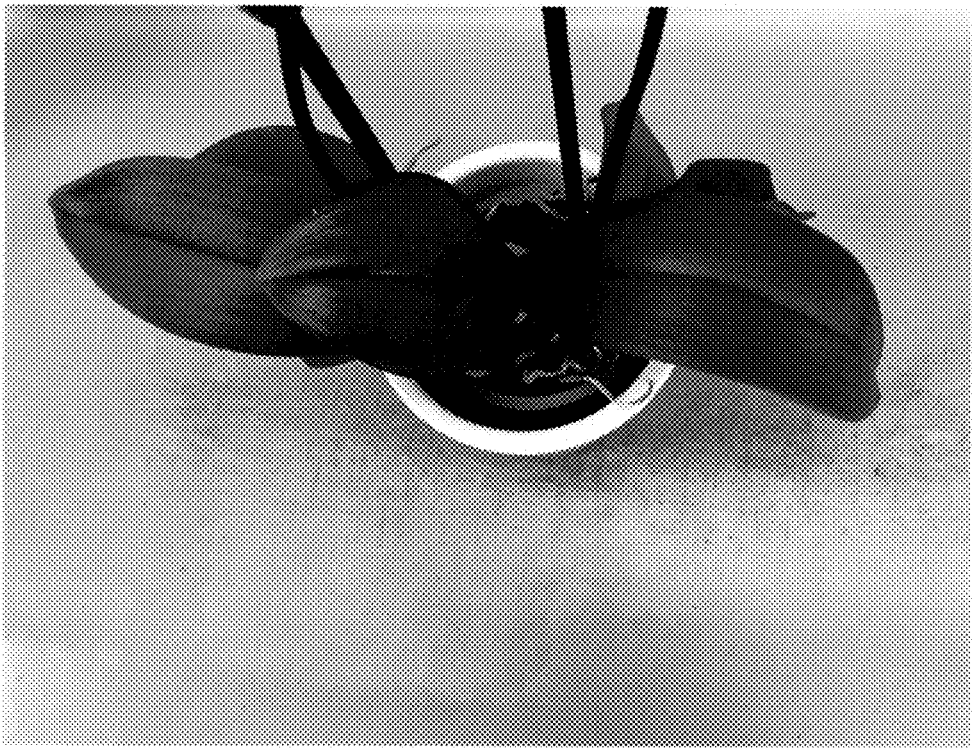
FIG. 3 shows a close-up, overhead view of the leaves of 'PHA777638'.

The following detailed description sets forth the distinctive characteristics of 'PHA777638'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is the R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHA777638'.

Parentage:

*Female parent.*—*Phalaenopsis* cultivar '00001-4992' (unpatented).

*Male parent.*—*Phalaenopsis* cultivar 'PHALLOEL' (unpatented).

Propagation:

*Type.*—Meristem tissue culture.

Roots:

*Root description.*—Greyed-green colored roots (a color in between RHS 190B and RHS 190C) with branching lateral roots having yellow-green (RHS 146D) colored root tips.

Plant:

*Crop time to flowering.*—Following asexual propagation (in vitro), the rooted cuttings grow for 20-24 weeks. After transplantation into 12-cm, pots, the plants are finished after 48 to 50 weeks.

*Growth habit of the peduncle.*—Upright to slightly pendent with panicle and raceme inflorescence.

*Height* (*from soil level to top of inflorescence*).—Approximately 59.0 cm to 64.0 cm.

*Width* (*measured from leaf tips*).—About 35.0 cm to 37.0 cm.

*Vigor.*—Strong.

Leaves:

*Mature leaves.*—Quantity per plant: 9 to 10 leaves are produced before flowering. Length (fully expanded): 19.0 cm to 21.0 cm. Width: 6.0 cm to 7.0 cm. Position of the broadest part of the leaf: At the middle. Shape: Oblong. Base shape: Moderately elongated. Apex: Obtuse asymmetric. Leaf blade angle with the petiole (measured from the horizontal position): Between 25 degrees and 40 degrees. Leaf margin: Entire. Color: Upper surface: RHS 146A with a small brown margin (RHS 200C) toward the tip. Lower surface: RHS 146B with a purple margin (RHS N77A) toward the tip. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B.

Peduncle:

*Quantity per plant.*—2.

*Number of flowers per peduncle.*—15 to 25.

*Length.*—59.0 cm to 64.0 cm.

*Diameter.*—5.0 mm to 6.0 mm.

*Strength.*—Strong.

*Aspect.*—Upright to slightly pendent.

*Texture.*—Smooth.

*Color.*—Brown (RHS 200A) with a touch of light green (RHS 195A).

*Internode length.*—3.5 cm to 5.5 cm.

Inflorescence description:

*Appearance.*—Upright to slightly pendent, panicle and raceme inflorescence with bilaterally symmetrical flowers that open in succession beginning with the lowermost flower.

*Number of inflorescences.*—2.

*Inflorescence size.*—Height (from base to tip): 330.0 mm to 430.0 mm.

*Flowering time.*—First flowers can be expected 10 to 11 months after planting in a 12-cm pot.

*Flower.*—Height: 75.0 mm to 80.0 mm. Diameter: 85.0 mm to 90.0 mm. Depth of lip: 22.0 mm to 24.0 mm.

*Flower shape.*—Flat.

*Flower longevity.*—On the plant: 7 to 9 weeks.

*Fragrance.*—Absent.

*Flower bud.*—Average size: Medium to large. Length: 21.0 mm to 23.0 mm. Width: 17.0 mm to 19.0 mm. Shape: Egg shaped. Color: Touch of yellow-green (RHS 145B) at the base; dark purplish-red (a color in between RHS N79C and RHS N79D) toward the tip.

*Petals.*—Arrangement: Open/free. Shape: Moderately compressed to medium. Apex: Emarginated asymmetric. Margin: Moderately undulated. Length (from base to tip): 42.0 mm to 44.0 mm. Width: 52.0 mm to 54.0 mm. Position of the broadest part of the petal: Toward the base. Color (when fully opened): Upper surface: Basic color: Purplish-pink (RHS N78C). Over color: Light purple (RHS 76A); dotted at the base RHS N78A; shaded RHS N78B. Lower surface: Basic color: Purplish-pink (RHS N78C). Over color: A touch of very light purple (RHS 76B) at the base and reddish-purple (RHS N78B) on sides. Number of spots, dots, and stripes on the petals (upper surface): Medium number of very small dots. Color of spots, dots, and stripes on the petals (upper surface): RHS N78A. Density of netting of the petals (upper surface): None. Color of the netting (upper surface): Not applicable.

*Dorsal sepal.*—Shape: Elliptic. Apex: Emarginated symmetric. Margin: Entire. Length (from base to tip): 41.0 mm to 43.0 mm. Width: 26.0 mm to 28.0 mm. Position of the broadest part of the dorsal sepals: At the middle. Color (when fully opened): Upper surface: Basic color: Reddish-purple (RHS N78B). Over color: Very light purple dots (RHS 76B); reddish-purple shade and netting (RHS N78B). Lower surface: Basic color: Reddish-purple (RHS N78B). Over color: Light yellow-green (RHS 145D) and very light purple dots (RHS 76C). Number of spots, dots, and stripes on the dorsal sepals (upper surface): Very many of very small dots. Color of spots, dots, and stripes on the dorsal sepals (upper surface): RHS 76B. Density of netting of the dorsal sepals (upper surface): Very low. Color of the netting: RHS N78B.

*Lateral sepals.*—Shape: Ovate. Apex: Obtuse asymmetric. Margin: Entire. Length (from base to tip): 42.0 mm to 44.0 mm. Width: 24.0 mm to 26.0 mm. Position of the broadest part of the lateral sepals: Toward the base. Color (when fully opened): Upper surface: Basic color: Reddish-purple (RHS N78B). Over color: Light yellow-green (RHS 145D) with small purplish-red dots (RHS 64A) at the base; very small number of very light purple dots (RHS 76B) scattered all over sepal. Lower surface: Basic color: Reddish-purple (RHS N78B). Over color: Light yellow-green (RHS 145D) at the base; very light purple dots (RHS 76C). Number of spots, dots, and stripes on the lateral sepals (upper surface): Medium number of small dots and very many of very small spots. Color of spots, dots, and stripes on the lateral sepals (upper surface): Small dots RHS 64A and very small dots RHS 76B. Density of netting of the lateral sepals (upper surface): None. Color of the netting (upper surface): Not applicable.

*Labellum* (*lip*).—Whiskers: Present. Length of whiskers: 13.0 mm to 15.0 mm. Color of whiskers: Reddish-purple (RHS N78B) with white tips (RHS NN155C). Pubescence on the lip: Absent.

*Lateral lobe.*—Shape: Type V (as described in the International Union for the Protection of New Varieties of Plants (UPOV) Test Guidelines for *Phalaenopsis*); spatulate. Margin: Moderately undulated. Length: 23.0 mm to 25.0 mm. Width: 15.0 mm to 17.0 mm. Color: Upper surface: White (RHS NN155C) with a touch of yellow (RHS 5D) and stripes (RHS 178B) at the base; light reddish-purple (RHS N78D) and shaded RHS N78B toward the margins. Lower surface: White (RHS NN155C) on one side at the base; purplish-pink (RHS N78C) on the other side; reddish-purple (RHS N78B) toward the tips and other margin. Number of spots and stripes on the lateral lobe: Few stripes. Color of spots and stripes on the lateral lobe: RHS 178B. Density of netting of the lateral lobe: None. Color of the netting: None.

*Apical lobe.*—Shape: Trullate. Margin: Entire. Length: 22.0 mm to 24.0 mm. Width: 21.0 mm to 23.0 mm. Color: Upper surface: Light greenish-yellow margin (RHS 7D) and spotted RHS 178B at the base; reddish-purple (RHS N78B) toward the whiskers. Lower surface: Reddish-purple (RHS N78A). Number of spots and stripes on the apical lobe: Few spots. Color of spots and stripes on the apical lobe: RHS 178B. Density of netting of the apical lobe: None. Color of the netting: None. Bump and ridge (upper and lower surface): Not present.

*Callus.*—Average size: Medium. Height: 7.0 mm to 8.0 mm. Length: 5.0 mm to 6.0 mm. Width: 4.0 mm to 5.0 mm. Color: Greenish-yellow (RHS 7C), dotted RHS 59B; yellowish-white (RHS NN155A) on sides.

Reproductive organs:

*Column.*—Length: 10.0 mm to 11.0 mm. Diameter: 4.0 mm to 5.0 mm. Color: White (RHS NN155D) at the base; purplish-pink (RHS N78C) toward tips.

*Pollinia.*—Quantity: 2. Diameter: 1.0 mm to 1.2 mm. Color: Orange (RHS 24A).

*Ovary.*—Length: 10.0 mm to 12.0 mm. Diameter: 2.1 mm to 2.4 mm.

*Pedicel.*—Length: 37.0 mm to 39.0 mm. Diameter: 2.5 mm to 2.8 mm. Color: Touch of dark red (RHS N186D) at the base; light yellow-green (RHS 195B); light purple (RHS 76A) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA777638' differs from the female parent plant, cultivar '00001-4992' (unpatented), in that 'PHA777638' has trullate apical lobes and petals that are moderately to medium compressed, whereas '00001-4992' has triangular apical lobes and petals that are moderately compressed.

'PHA777638' differs from the male parent plant, cultivar 'PHALLOEL' (unpatented), in that 'PHA777638' has a medium number of spots on the petals with no stripes on the petals and the apex of the dorsal sepal is emarginated, whereas 'PHALLOEL' does not have any spots on the petals, but a medium number of stripes on the petals and the apex of the dorsal sepal is obtuse.

'PHA777638' is most similar to the commercial *Phalaenopsis* plants named 'PHA441188' (U.S. Plant Pat. No. PP34,942) and 'PHALGEXPA' (U.S. Plant Pat. No. PP30,436). 'PHA777638' differs from the commercial variety 'PHA441188' in that 'PHA777638' has trullate apical lobes and no stripes on the apical lobes, and short to medium whiskers, whereas 'PHA441188' has rhombic apical lobes having many stripes on apical lobes, and very short to short whiskers. Additionally, 'PHA777638' has a medium number of spots and no stripes on the petals, whereas 'PHA441188' has many stripes on the petals, but no spots.

'PHA777638' differs from the commercial variety 'PHALGEXPA' in that 'PHA777638' has strong curvature of the lateral lobes, whereas 'PHALGEXPAI' has medium curvature of the lateral lobes. Additionally, 'PHA777638' has trullate apical lobes, whereas 'PHALGEXPA' has triangular apical lobes.

I claim:

1. A new and distinct variety of *Phalaenopsis* plant named 'PHA777638', substantially as described and illustrated herein.

* * * * *